United States Patent [19]
Bhattacharyya

[11] 4,155,244
[45] May 22, 1979

[54] APPARATUS FOR DETERMINING THERMAL CONDUCTIVITY OF MATERIALS

[75] Inventor: Rabindra K. Bhattacharyya, Newark, Ohio

[73] Assignee: Owens-Corning Fiberglas Corporation, Toledo, Ohio

[21] Appl. No.: 866,109

[22] Filed: Dec. 30, 1977

[51] Int. Cl.² ............................................. G01F 25/18
[52] U.S. Cl. ................................................... 73/15 A
[58] Field of Search ............................... 73/15 A, 1 F

[56] References Cited
U.S. PATENT DOCUMENTS

| 2,484,736 | 10/1949 | Razek | 73/15 |
| 3,045,473 | 7/1962 | Hager, Jr. | 73/15 |
| 3,075,377 | 1/1963 | Lang | 73/15 |
| 3,552,185 | 1/1971 | Goode, Jr. et al. | 73/15 |

*Primary Examiner*—Herbert Goldstein
*Attorney, Agent, or Firm*—Ronald C. Hudgens; Philip R. Cloutier; Ted C. Gillespie

[57] ABSTRACT

A method and apparatus for measuring thermal conductivity of materials is provided. A test specimen is placed intermediate a hot plate and a cold plate, and a heat flow sensing means is placed intermediate the material to form two portions of the test specimen. A guarded hot plate measurement of the heat flow to the hot plate enables calibration of the sensitivity of the specimens and the heat flow sensing means. The apparatus is then calibrated for measurement of other specimens of like physical properties.

7 Claims, 1 Drawing Figure

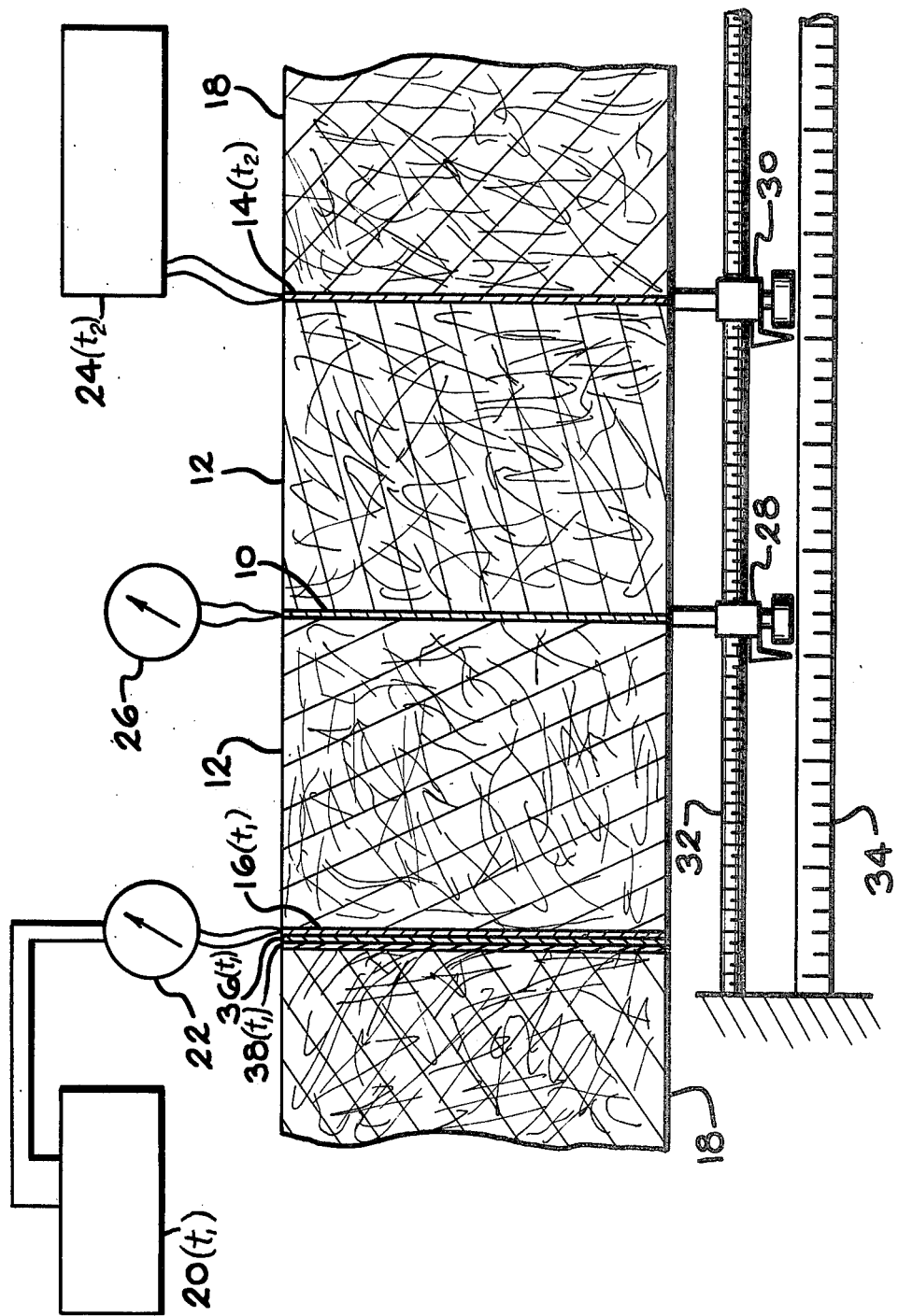

APPARATUS FOR DETERMINING THERMAL CONDUCTIVITY OF MATERIALS

This invention relates to the method and apparatus for determining the thermal conductivity of materials. More specifically, it pertains to determining the thermal conductivity of materials, such as insulative materials in a relatively short time.

One well known testing method and apparatus, known in the art as the guarded hot plate, is disclosed in ASTM C 177-71. Using a guarded hot plate, a test specimen is placed between two cold plates. The specimen is divided into halves by a hot plate which is approximately parallel to the two cold plates. The temperature of the hot plate is set at $t_1$ and maintained at $t_1$ by the input of heat q. The temperature of the cold plates is maintained at $t_2$, which is lower than $t_1$. The apparatus and the specimen are allowed to come to steady state, at which point the heat, q, necessary to maintain the hot plate at $t_1$ equals the heat flow from the hot plate to the cold plates. Since the thickness, L, of the specimen and the area of the plates, A, are known quantities, the conductivity of the specimen can be calculated using the relationship $$= qL/A(t_1 - t_2)$$

The guarded hot plate is able to measure conductivities of specimens having various values of density and various thicknesses. The guarded hot plate has a high degree of accuracy because of the assurance of the unidimensionality of the heat flow from the hot plate to the cold plates. Unfortunately, the guarded hot plate takes a relatively long time to come to steady state—usually up to 4 hours or more—and therefore it is not useful for rapid monitoring of an insulation manufacturing process. Also, the guarded hot plate requires bulky and expensive equipment and the handling of a skilled operator. Additionally, the guarded hot plate measures the average conductivity of two insulating slabs in parallel, rather than the conductivity of a single slab. The difference between these two conductivities is especially significant when radiative heat transfer is substantial.

Another method and apparatus commonly used for measuring thermal conductivity is the heat flow meter, described in ASTM C 518-70. In this instrument, a heat flow transducer is sandwiched between two slabs of insulating materials and this entire assembly is inserted between a hot and a cold plate. The principle of the instrument is based on the assumption that during steady state, heat flow through the transducer is the same as that through the two slabs with the transducer. Thus if the conductivity of the transducer material is K, the thickness is $L_T$ and the transducer output showing the temperature difference across the transducer is $D_t$ then the effective thermal conductivity $K_{eff}$ of the two slabs with the transducer is $$K_{eff} = K \times (D_t/L_T) \times [L_s/(t_1 - t_2)]$$

where $L_s$ is the combined thickness of the two slabs with the transducer and $t_1$ and $t_2$ are the hot and cold plate temperatures respectively. The variables K, $L_T$, and $(t_1 - t_2)$ are often combined into one factor and the effective conductivity is written as $F \times D_t \times L_s$. Here F (often called the "box factor") is calculated by testing two insulating slabs, the conductivity of the slabs having been determined by testing the slabs in the guarded hot plate.

The heat flow meter has advantages over the guarded hot plate in that it is not as dependent on the room temperature and it does not require a highly skilled operator. The primary advantage of the heat flow meter is the speed at which the test can be made, some tests being run in less than one half hour. It is to be noted, however, that neither of the above instruments measures the effective conductivity of a single slab of insulating material. While the guarded hot plate measures the average conductivity of two slabs in parallel, the heat flow meter is set up in an attempt to measure the average conductivity of two slabs placed in series with the heat flow transducer. Since the object is to calculate the conductivity of a single slab of insulating material, neither of the above instruments satisfies the requirement. Calculating F by equating the two conductivity values is invalid since the heat flow meter and guarded hot plate measure two different quantities.

There has now been developed for measuring thermal conductivities of materials a method and apparatus which combines the advantages of both the guarded hot plate and the heat flow meter. The method and apparatus of this invention utilize the beneficial qualities of the guarded hot plate to measure the box factor F of the particular heat flow meter and therefore to calibrate the meter. The beneficial qualities of the heat flow meter for rapid and simple testing are also utilized. The apparatus is calibrated by placing a test specimen in between a hot plate and a cold plate. Upon reaching steady state the quantity of heat input q to the hot plate will indicate the heat transfer rate through the specimen. A heat flow sensing means, or transducer, is then placed intermediate the test specimen, and the heat flow is determined by the transducer. The two values are compared and the box factor F can be calculated. Once the heat flow instrument has been calibrated, other test specimens can be placed in the apparatus, provided they are of like physical properties (taking into account such properties as thickness, density, glass composition, fiber orientation and binder composition.) The heat flow sensing means placed intermediate the pack can be of the type in which heat flow is measured by determining the electromotive force passing through a transducer. The hot and cold members can be doubly guarded to eliminate heat transfer to or from external sources. The hot and cold members can be movable to accommodate different thicknesses of test specimens, in which case a means can be provided for measuring the distances between the various elements of the apparatus. The hot member can be adapted to provide substantially unidirectional heat flow in the direction of the cold plate.

According to this invention there is provided apparatus for measuring heat flow through a medium comprising a first member at a first temperature; a second member at a second temperature less than the first temperature, the first and second members being adapted for the positioning of the medium therebetween; means for maintaining the temperature of the second member at a constant; means for ensuring substantially unidirectional heat flow from the first member; heat flow sensing means adapted to be positioned within the medium to measure heat flow from the first member to the second member; means for supplying heat to the first member to maintain the temperature of the first member at a constant; and, means for measuring heat flow from the means for supplying heat to the first member. The heat flow sensing means can be a means for determining the electromotive force generated by heat flow through a transducer. The first member and second member can be doubly guarded. There can be provided means for adjusting the distance between the heat flow sensing means and either the first member or the second member or both. There can be means provided for measuring the distance between the first member and the second member.

Also, according to this invention, there is provided a method for measuring heat flow through a medium comprising positioning a heat flow sensing means within the medium; positioning the medium between a first member and a second member; maintaining the temperatures of the said first member and the second member at constants, the temperature of the first member being higher than the temperature of the second member; measuring the heat flow from a means for supplying heat to the first member to calibrate the heat flow sensing means; and, measuring the heat flow from the first member to the second member with the heat flow sensing means. The heat flow sensing means can be positioned substantially at the mid point of the thickness of the medium. The measuring of the heat flow with the heat flow sensing means can comprise determining the magnitude of the electromotive force generated by the heat flow through a transducer.

The method and apparatus of this invention are particularly suitable for measuring the conductivity of insulation blankets of fibrous glass.

This invention will be more fully understood by reference to the drawing in which the invention is shown schematically. Two specimen portions 12 are positioned between first member 16, hereinafter the hot plate, and second member 14, hereinafter the cold plate. The second member can also be any heat sink, including the atmosphere. Heat flow sensing means 10 is placed between the specimen portions. In the preferred embodiment, the heat flow sensing means is a transducer, and the thermal gradient established through the transducer generates an electromotive force which can be measured by any suitable device such as EMF meter 26. Insulation 18 is provided adjacent the cold plate and hot plate. The hot and cold plates can both be doubly guarded to ensure uniformity of temperature over the test section and increase the probability of one-dimensional heat flow. In order to provide substantially unidirectional heat flow null meter 36 and heater 38 are positioned adjacent the hot plate. The heater is maintained at temperature $t_1$ by conventional means, not shown; and the null meter indicates the condition in which there is zero heat transfer between the hot plate and the heater. The null meter ensures the unidirectionality of heat flow from the hot plate since heat will not be transferred in the direction of the heater when the temperatures of the hot plate and the heater are the same. Heat is supplied from heat source 20, which can be any conventional means for supplying heat, to the hot plate to maintain the hot plate at a constant temperature. Q Meter 22 measures the heat input q from the heat source to the hot plate. Heat sink 24 is adapted to remove heat from the cold plate to maintain the temperature of the cold plate at a constant, $t_2$.

In practice the specimen halves are placed between the hot plate and the cold plate without the transducer, and the apparatus is allowed to come to a steady state. At steady state, the heat flow from the heat source to the hot plate will be a measure of the heat flow from the hot plate to the cold plate. This gives the effective conductivity of the specimen. Thus, at steady state, the heat flow through the transducer is the same as that measured using the Q meter. Next, the transducer is inserted between the specimen halves. The heat flow through the transducer is measured, and compared with the effective conductivity of the specimen without the transducer. The comparison of the two quantities allows the calculation of the box factor F, and the EMF meter can be calibrated.

Once the heat flow meter is calibrated for a particular specimen density and thickness, other specimens of like thickness and density can be placed in the apparatus of this invention for thermal conductivity measurement. The apparatus will not require further calibration, and rapid tests can be made.

It is possible for the meter of this invention to be pre-calibrated by establishing a calibration curve which gives values of the box factor F for various values of specimen thickness. A family of curves can be provided to indicate values of F for specimens of different densities, mean temperatures, and other physical properties.

In order to accommodate different thicknesses of insulation, portions of the apparatus are mounted for movement relative to other portions of the apparatus. As shown in the drawing both the heat flow meter plate and the cold plate can be adapted with mounting means 28 and 30, respectively, which are movable on track 32. The positioning of the heat flow meter plate and the cold plate along the track enable the apparatus to accommodate unlike thicknesses of insulation specimens. Scale 34 allows an operator to measure the distances between various elements of the apparatus, such as the distance between the hot plate and the cold plate.

In order to accommodate the measuring of the thermal conductivities of samples where heat transfer is substantially non-horizontal (e.g. attic insulation) the apparatus of this invention can be adapted to be tilted to various orientations, including an orientation in which the plates are horizontal.

It will be evident that various modifications can be made to this invention. Such, however, are considered as being within the scope of the invention.

I claim:

1. Apparatus for measuring thermal conductivity comprising:
   a. a first member at a first temperature;
   b. means for ensuring substantially unidirectional heat flow from said first member;
   c. a second member at a second temperature less than the first temperature, said first and second members being adapted for the positioning of a medium therebetween;
   d. means for maintaining the temperature of said second member at a constant;
   e. heat flow sensing means adapted to be positioned within said medium to measure heat flow from said first member to said second member;
   f. means for supplying heat to said first member to maintain the temperature of said first member at a constant; and
   g. means for measuring heat flow from said means for supplying heat to said first member.

2. The apparatus of claim 1 in which said heat flow sensing means comprises means for determining the electromotive force generated by heat flow through a transducer.

3. The apparatus of claim 2 comprising means for measuring the distance between said first member and said second member.

4. The apparatus of claim 3 comprising means for adjusting the distance between said heat flow sensing means and either said first member or said second member.

5. The method of measuring thermal conductivity comprising:
   a. positioning a heat flow sensing means within a medium;
   b. positioning said medium between a first member and a second member;
   c. maintaining temperatures of said first member and said second member constant the temperature of said first member being greater than the temperature of said second member;
   d. measuring heat flow from a means for supplying heat to said first member to calibrate said heat flow sensing means; and,
   e. measuring heat flow from said first member to said second member with said heat flow sensing means.

6. The method of claim 5 in which measuring the heat flow with said heat flow sensing means comprises determining the magnitude of the electromotive force generated by heat flow through a transducer.

7. The method of claim 6 comprising positioning said heat flow sensing means substantially at the midpoint of the thickness of said medium.

* * * * *